(12) United States Patent
Gilges et al.

(10) Patent No.: US 6,413,490 B1
(45) Date of Patent: Jul. 2, 2002

(54) GRANULES BASED ON PYROGENIC TITANIUM DIOXIDE AND A PROCESS FOR PREPARING THE GRANULES

(75) Inventors: Hilmar Gilges, Aschaffenburg; Dieter Kerner, Hanau; Jürgen Meyer, Stockstadt/Main, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/599,889

(22) Filed: Jun. 23, 2000

Related U.S. Application Data
(60) Provisional application No. 60/140,794, filed on Jun. 25, 1999.

(30) Foreign Application Priority Data

Jun. 24, 1999 (DE) .......................................... 199 28 851

(51) Int. Cl.$^7$ .......................................... C01G 23/047
(52) U.S. Cl. ..................................................... 423/610
(58) Field of Search ............................... 423/610, 611, 423/612, 613; 502/350, 439

(56) References Cited

U.S. PATENT DOCUMENTS

| | | | |
|---|---|---|---|
| 4,364,515 A | * 12/1982 | Prussin ........................ | 239/8 |
| 5,237,019 A | * 8/1993 | Wieland et al. ............. | 525/475 |
| 5,372,905 A | 12/1994 | Deusser | |
| 5,415,936 A | 5/1995 | Deusser | |
| 6,193,795 B1 | * 2/2001 | Nargiello et al. ........... | 106/484 |
| 6,239,194 B1 | * 5/2001 | Standke et al. ............. | 523/200 |

FOREIGN PATENT DOCUMENTS

| | | |
|---|---|---|
| DE | 42 02 695 | 8/1993 |
| WO | WO 98/11037 | 3/1998 |

* cited by examiner

*Primary Examiner*—Steven P. Griffin
*Assistant Examiner*—Edward Johnson
(74) *Attorney, Agent, or Firm*—Pillsbury Winthrop LLP

(57) ABSTRACT

Granules based on titanium dioxide with the characteristics:
- Average particle diameter: 10 to 150 μm
- BET surface area: 25 to 100 m$^2$/g
- pH: 3 to 6
- Compacted density: 400 to 1,200 g/l The granules are prepared by dispersing titanium dioxide in water, spray-drying and silanizing. In the silanized form, the granules have the following characteristics:
- Average particle diameter: 10 to 160 μm
- BET surface area: 15 to 100 m$^2$/g
- pH: 3.0 to 9.0
- Compacted density: 400 to 1,200 g/l
- Carbon content: 0.3 to 12.0 wt. %

The granules are used, inter alia, as catalyst supports, in cosmetics, as sun screens, in silicone rubber, in toning powder, in lacquers and colorants, as grinding and polishing agents and as a raw material for producing glass and ceramics.

6 Claims, No Drawings

GRANULES BASED ON PYROGENIC TITANIUM DIOXIDE AND A PROCESS FOR PREPARING THE GRANULES

This application is based on German Application No. 19928851.8, filed Jun. 24, 1999, and on U.S. Provisional Application No. 60/140,794, filed Jun. 25, 1999, which disclosures are incorporated herein by reference.

FIELD OF THE INVENTION

The invention provides granules based on pyrogenic titanium dioxide, a process for preparing the granules, and the use thereof.

BACKGROUND OF THE INVENTION

It is known that pyrogenic titanium dioxide can be prepared from $TiCl_4$ by high temperature or flame hydrolysis (Ullmanns Enzyklopädie der Technischen Chemie, 4th edition, vol. 21, page 464 (1982)).

Pyrogenic titanium dioxide is characterized by extremely finely divided particles, a high surface area (BET), very high purity, spherically shaped particles and a lack of pores. As a result of these properties, pyrogenic titanium dioxide is increasingly being considered as a support for catalysts (Dr. Koth et al., Chem. Ing. Techn. 52, 628 (1980)). For this application, pyrogenic titanium dioxide is shaped in a mechanical manner using, for example, tabletting machines.

SUMMARY OF THE INVENTION

The object of the invention is to produce spray-dried granules of pyrogenic titanium dioxide which can be used as a catalyst support.

The invention provides granules based on pyrogenic titanium dioxide with the following physico-chemical characteristics:

Average particle diameter: 10 to 150 $\mu m$

BET surface area: 25 to 100 $m^2/g$ pH: 3 to 6

Compacted density: 400 to 1,200 g/l

Granules according to the invention can be prepared by dispersing pyrogenic titanium dioxide in water and then spray-drying.

The invention also provides granules based on pyrogenic titanium dioxide with the following physico-chemical characteristics:

Average particle diameter: 10 to 160 $\mu m$

BET surface area: 15 to 100 $m^2/g$ pH: 3.0 to 9.0

Compacted density: 400 to 1,200 g/l

Carbon content: 0.3 to 12.0 wt. %

Granules according to the invention can be prepared by dispersing pyrogenic titanium dioxide in water, spray-drying and then silanizing the product. Halogenated silanes, alkoxysilanes, silazanes and/or siloxanes are used for silanizing.

The following substances may be used in particular as halogenated silanes:

Halogenated organosilanes of the type $X_3Si(C_nH_{2n+1})$

X=Cl, Br n=1–20.

Halogenated organosilanes of the type $X_2(R')Si(C_nH_{2n+1})$

X=Cl, Br

R'=alkyl n=1–20.

Halogenated organosilanes of the type $X(R')_2Si(C_nH_{2n+1})$

X=Cl, Br

R'=alkyl n=1–20.

Halogenated organosilanes of the type $X_3Si(CH_2)_m$—R'

X=Cl, Br m=0, 1–20

R'=alkyl, aryl (e.g. —$C_6H_5$)

—$C_4F_9$, —$OCF_2$—CHF—$CF_3$, —$C_6F_{13}$, —O—$CF_2$—$CHF_2$

—$NH_2$, —$N_3$, —SCN, —CH=$CH_2$,

—$OOC(CH_3)C=CH_2$

—$OCH_2$—$CH(O)CH_2$

—NH—CO—N—CO—$(CH_2)_5$

—NH—COO—$CH_3$, —NH—COO—$CH_2$—$CH_3$,

—NH—$(CH_2)_3Si(OR)_3$

—$S_x$—$(CH_2)_3Si(OR)_3$, where R is alkyl.

Halogenated organosilanes of the type $(R)X_2Si(CH_2)_m$—R'

X=Cl, Br

R=alkyl m=0, 1–20

R'=alkyl, aryl (e.g. —$C_6H_5$)

—$C_4F_9$, —$OCF_2$—CHF—$CF_3$, —$C_6F_{13}$, —O—$CF_2$—$CHF_2$

—$NH_2$, —$N_3$, —SCN, —CH=$CH_2$,

—$OOC(CH_3)C=CH_2$

—$OCH_2$—$CH(O)CH_2$

—NH—CO—N—CO—$(CH_2)_5$

—NH—COO—$CH_3$, —NH—COO—$CH_2$—$CH_3$,

—NH—$(CH_2)_3Si(OR)_3$

—$S_x$—$(CH_2)_3Si(OR)_3$, where R is alkyl.

Halogenated organosilanes of the type $(R)_2XSi(CH_2)_m$—R'

X=Cl, Br

R=alkyl m=0, 1–20

R'=alkyl, aryl (e.g. —$C_6H_5$)

—$C_4F_9$, —$OCF_2$—CHF—$CF_3$, —$C_6F_{13}$, —O—$CF_2$—$CHF_2$

—$NH_2$, —$N_3$, —SCN, —CH=$CH_2$,

—$OOC(CH_3)C=CH_2$

—$OCH_2$—$CH(O)CH_2$

—NH—CO—N—CO—$(CH_2)_5$

—NH—COO—$CH_3$, —NH—COO—$CH_2$—$CH_3$,

—NH—$(CH_2)_3Si(OR)_3$

—$S_x$—$(CH_2)_3Si(OR)_3$, where R is alkyl.

The following substances may be used in particular as alkoxysilanes:

Organosilanes of the type $(RO)_3Si(C_nH_{2n+1})$

R=alkyl n=1–20

Organosilanes of the type $R'_x(RO)_ySi(C_nH_{2n+1})$

R=alkyl

R=alkyl n=1–20 x+y=3 x=1, 2 y=1, 2

Organosilanes of the type $(RO)_3Si(CH_2)_m$—R

R=alkyl m=0, 1–20

R'=alkyl, aryl (e.g. —$C_6H_5$)
 —$C_4F_9$, —$OCF_2$—CHF—$CF_3$, —$C_6F_{13}$, —O—$CF_2$—$CHF_2$
 —$NH_2$, —$N_3$, —SCN, —CH=$CH_2$,
 —OOC($CH_3$)C=$CH_2$
 —$OCH_2$—CH(O)$CH_2$
 —NH—CO—N—CO—$(CH_2)_5$
 —NH—COO—$CH_3$, —NH—COO—$CH_2$—$CH_3$,
 —NH—$(CH_2)_3$Si$(OR)_3$
 —$S_x$—$(CH_2)_3$Si$(OR)_3$ Organosilanes of the type $(R'')_x(RO)_y Si(CH_2)_m$—R'

R=alkyl m=0, 1–20

R"=alkyl x+y=3
 x=1, 2
 y=1, 2

R'=alkyl, aryl (e.g. —$C_6H_5$)
 —$C_4F_9$, —$OCF_2$—CHF—$CF_3$, —$C_6F_{13}$, —O—$CF_2$—$CHF_2$
 —$NH_2$, —$N_3$, —SCN, —CH=$CH_2$,
 —OOC($CH_3$)C=$CH_2$
 —$OCH_2$—CH(O)$CH_2$
 —NH—CO—N—CO—$(CH_2)_5$
 —NH—COO—$CH_3$, —NH—COO—$CH_2$—$CH_3$,
 —NH—$(CH_2)_3$Si$(OR)_3$
 —$S_x$—$(CH_2)_3$Si$(OR)_3$ The silane Si 108 [$(CH_3O)_3$—Si—$C_8H_{17}$] trimethoxyoctylsilane is preferably used as a silanizing agent.

The following substances may be used in particular as silazanes:

Silazanes of the type

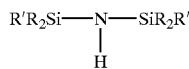

R=alkyl

R'alkyl, vinyl and also, for example, hexamethyldisilazane.

The following substances may be used in particular as siloxanes:

Cyclic polysiloxanes of the types D 3, D 4, D 5, e.g. hexamethylcyclotrisiloxane=D 3

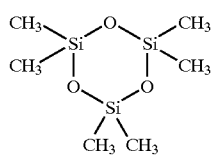

e.g. octamethylcyclotetrasiloxane=D 4

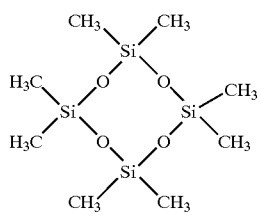

e.g. decamethylcyclopentasiloxane=D 5

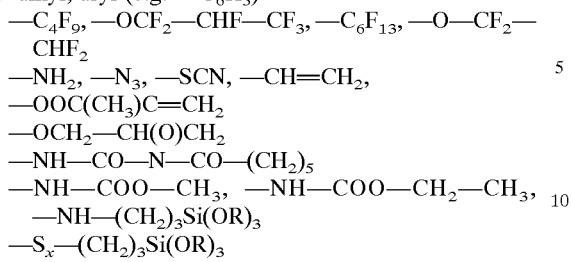

Polysiloxanes or silicone oils of the type

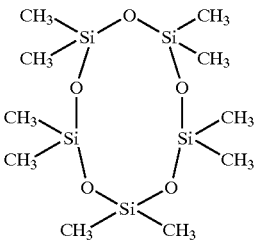

m = 0, 1, 2, 3, ... ∞
n = 0, 1, 2, 3, ... ∞
u = 0, 1, 2, 3, ... ∞

Y=$CH_3$, H, $C_nH_{2n+1}$, n=1–20
$y^1$=Si$(CH_3)_3$, Si$(CH_3)_2$H
 Si$(CH_3)_2$OH, Si$(CH_3)_2$($OCH_3$)
 Si$(CH_3)_2$($C_nH_{2n+1}$), n=1–20
R=alkyl, aryl, $(CH_2)_n$—$NH_2$, H
R'=alkyl, aryl, $(CH_2)_n$—$NH_2$, H
R"=alkyl, aryl, $(CH_2)_n$—$NH_2$, H
R'"=alkyl, aryl, $(CH_2)_n$—$NH_2$, H The carbon content of granules according to the invention may be 0.3 to 12.0 wt. %.

The dispersion in water may have a titanium dioxide concentration of 3 to 25 wt. %.

Organic auxiliary substances may be added to the dispersion in order to increase the stability of the dispersion and to improve the particle morphology after spray-drying.

The following auxiliary substances may be used, for example:
 polyalcohols, polyethers, surfactants based on fluorinated hydrocarbons, alcohols.

Spray-drying may be performed at a temperature of 200° to 600° C. Spinning disc atomizers or nozzle atomizers may be used.

Silanizing may be performed using the halogenated silanes, alkoxysilanes, silazanes and/or siloxanes described above, wherein the silanizing agent may optionally be dissolved in an organic solvent such as, for example, ethanol.

The silane Si 108 [$(CH_3O)_3$—Si—$C_8H_{17}$] trimethoxyoctylsilane may preferably be used as the silanizing agent.

Silanizing may be performed by spraying the granules with silanizing agent at room temperature and then thermally treating the mixture at a temperature of 105° to 400° C. for a period of 1 to 6 hours.

An alternative method of silanizing the granules may be performed by treating the granules with the silanizing agent in vapor form and then thermally treating the mixture at a temperature of 200° to 800° C. for a period of 0.5 to 6 hours.

Thermal treatment may be performed under a protective gas such as, for example, nitrogen.

Silanizing may be performed continuously or batchwise in heatable mixers and dryers with spray devices. Suitable devices may be, for example: plough bar mixers, disc dryers, fluidized bed dryers or moving bed dryers.

The physico-chemical parameters of the granules, such as the specific surface area, particle size distribution, compacted density and pH, may be modified within the limits given above by varying the substances used and the conditions used during spraying, heating at constant temperature and silanizing.

Titanium dioxide granules according to the invention have the following advantages:

The flow behavior is better than non-spray-dried titanium dioxide.

Incorporation into organic systems is easier. Dispersion is simpler.

No additional auxiliary substances are required for granulation.

Titanium dioxide granules according to the invention have a defined particle size, unlike non-spray-dried titanium dioxide which does not have a defined agglomerate size. Titanium dioxide granules according to the invention can be handled in a dust-free manner.

Lower packaging costs are required for transportation due to the high compacted density.

Titanium dioxide granules according to the invention can be used as a catalyst support.

Non-spray-dried titanium dioxide is not suitable for this purpose.

Granules according to the invention may be used as a support for catalysts, and also in cosmetics, as a sunscreen, in silicone rubber, in toning powder, in lacquers and colorants, as a grinding and polishing agent and as a raw material for producing glass and ceramics.

DETAILED DESCRIPTION OF THE PREFERRED EMBODIMENTS

EXAMPLES

A titanium dioxide P25 with the following physico-chemical characteristics is used as a pyrogenic titanium dioxide. It is disclosed in the series of documents called Pigments, no. 56 "Hochdisperse Metalloxide nach dem Aerosilverfahren", 4th edition, February 1989, Degussa AG.

|  | Titanium dioxide P25 |
|---|---|
| CAS no. | 13463-67-7 |
| Behavior in water | Hydrophilic |
| Appearance | loose white powder |
| BET surface area [1] $m^2/g$ | 50 ± 15 |
| Average size of primary Particles nm | 21 |
| Compacted density [2] g/l | about 100 |
| Specific weight [10] g/l | about 3.7 |
| Loss on drying [3] on leaving Supplier (2 h at 105° C.) % | <1.5 |
| Loss on ignition [4] [7] (2 h at 1000° C.) | <2 |
| pH [5] (in 4% aqueous dispersion) | 3–4 |
| $SiO_2$ [8] | <0.2% |
| $Al_2O_3$ [8] | <0.3% |
| $Fe_2O_3$ [8] | <0.01% |
| $TiO_2$ [8] | <99.5% |
| $ZrO_2$ [8] | — |
| $HfO_2$ [8] | — |
| HCl [9] | <0.3% |

| | Titanium dioxide P25 |
|---|---|
| Sieve residue [6] (Mockers method, 45 μm) % | <0.05% |

[1] according to DIN 661321
[2] according to DIN ISO 787/XI, JIS K 5101/18 (not sieved)
[3] according to DIN ISO 787/II, ASTM D 280, JIS K 5101/21
[4] according to DIN 55921, ASTM D 1208, JIS K 5101/23
[5] according to DIN ISO 787/IX; ASTM D 1208; JIS K 5101/24
[6] according to DIN ISO 787/XVIII; JIS K 5101/20
[7] with respect to substance dried for 2 h at 105° C.
[8] with respect to substance ignited for 2 h at 1000° C.
[9] HCl content is component of loss on ignition
[10] determined with an air comparison density bottle The titanium dioxides are prepared by spraying a volatile titanium compound into an oxyhydrogen flame formed from hydrogen and air. In most cases, titanium tetrachloride is used as the volatile titanium compound. This substance hydrolyzes under the effect of the water produced during the oxyhydrogen gas reaction to form titanium dioxide and hydrochloric acid. After leaving the flame, the titanium dioxide enters a so-called coagulation zone in which the titanium dioxide primary particles and primary aggregates agglomerate. The product, present at this stage as a kind of aerosol, is separated from the gaseous accompanying substances in cyclones and is then post-treated with moist hot air.

The particle sizes of the titanium dioxides may be varied by varying the reaction conditions such as, for example, temperature of the flame, proportion of hydrogen or oxygen, amount of titanium tetrachloride, residence time in the flame or the length of the coagulation zone.

The BET surface area is determined using nitrogen in accordance with DIN 66 131.

The compacted volume is determined in a similar way to that described in ASTM D 4164-88.

Equipment: Compacted volume meter STA V 2003 from the Engelsmann Co., in accordance with DIN53194, para. 5.2 b-f
250 ml measuring cylinder, graduation mark every 2 ml
Balance with maximum error limit of ±0.1 g.

Performing the Determination

Set the counter on the compacted volume meter to 1000 strokes.
Tare the measuring cylinder.
Fill measuring cylinder with granules up to the 250 ml mark.
Note down the weight (±0.1 g).
Clamp the measuring cylinder in the compacted volume meter and switch the instrument on.
The end of the compacting occurs when the instrument automatically stops after 1000 strokes.
Read the compacted bulk volume accurately, to 1 ml.

Calculation

E: weight of granules in g
V: volume read off in ml
W: water content in wt. % (determined in accordance with test instructions P001)

$$\text{Compacted density} = \frac{E \times (100 - W)}{V \times 100}$$

The pH is determined in 4% strength aqueous dispersion, and in the case of hydrophobic catalyst supports, in water-:ethanol 1:1.

Preparing Granules According to the Invention

The pyrogenic titanium dioxide is dispersed in fully deionized water. A dispersing apparatus is used which operates on the rotor/stator principle. The dispersions being produced are spray-dried. Deposition of the final product is achieved using a filter or a cyclone.

The spray-dried and optionally heated granules are initially introduced into a mixer to be silanized (hydrophobized) and are sprayed optionally first with water and then with the silanizing agent, under intense mixing. After completion of the spraying procedure, mixing is continued for 15 to 30 min and then the mixture is heated at a constant temperature of 100° to 400° C. for 1 to 4 hours.

The water used may be acidified with an acid, for example hydrochloric acid, until the pH is between 7 and 1. The silanizing agent used may be dissolved in a solvent such as, for example, ethanol,

TABLE 1

Data relating to spray-drying aqueous $TiO_2/P25$ dispersions

| Example | Amount of $H_2O$ [kg] | Amount of $TiO_2P25$ [kg] | Atomized using | Speed of atomizing disc [rpm] | Operating temp. [° C.] | Vent air temp. [° C.] | Deposition |
|---|---|---|---|---|---|---|---|
| 1 | 10 | 1.5 | Disc | 35 000 | 345 | 100 | cyclone |
| 2 | 10 | 1.5 | Disc | 45 000 | 370 | 105 | cyclone |
| 3 | 10 | 1.5 | Disc | 20 000 | 350 | 95 | cyclone |
| 4 | 10 | 2.5 | Disc | 15 000 | 348 | 100 | cyclone |
| 5 | 100 | 15 | 2-fluid nozzle | — | 445 | 130 | filter |
| 6 | 100 | 15 | Disc | 10 000 | 450 | 105 | filter |
| 7 | 10 | 2.5 | Disc | 20 000 | 348 | 105 | cyclone |
| 8 | 10 | 1.5 | Disc | 15 000 | 348 | 105 | cyclone |
| 9 | 10 | 2.5 | Disc | 35 000 | 300 | 105 | cyclone |

TABLE 2

Physico-chemical data of spray-dried products

| Example | BET surface area [m²/g] | Compacted density [g/l] | pH | $d_{50}$ value (Cilas) [μm] | Loss on drying [%] | Loss on ignition [%] |
|---|---|---|---|---|---|---|
| 1 | 51 | 641 | 3.9 | 14.6 | 0.9 | 0.9 |
| 2 | 50 | 612 | 3.7 | 10.6 | 0.8 | 1.0 |
| 3 | 52 | 680 | 3.5 | 25.0 | 0.8 | 1.0 |
| 4 | 51 | 710 | 3.7 | 43.6 | 0.8 | 1.2 |
| 5 | 52 | 660 | 4.0 | 17.1 | 0.9 | 0.9 |
| 6 | 53 | 702 | 3.9 | 27.5 | 0.9 | 0.9 |
| 7 | 50 | 708 | 3.5 | 26.7 | 1.1 | 0.6 |
| 8 | 53 | 696 | 3.9 | 30.1 | 1.0 | 0.9 |
| 9 | 49 | 640 | 3.7 | 16.0 | 0.7 | 0.8 |

TABLE 4

Physico-chemical data of hydrophobized titanium dioxide granules in accordance with Example 6

| Example | BET surface area [m²/g] | Carbon content [%] | Compacted density [g/l] | pH | Loss drying [%] |
|---|---|---|---|---|---|
| 10 | 36 | 3.9 | 848 | 3.1 | 0.2 |
| 11 | 30 | 5.5 | 873 | 3.2 | 0.4 |
| 12 | 32 | 2.1 | 768 | 3.6 | 0 |
| 13 | 25 | 3.3 | 883 | 3.9 | 0 |

What is claimed is:

1. Granules comprising pyrogenic titanium dioxide with the following physico-chemical characteristics:

Average particle diameter: 10 to 150 μm

BET surface area: 25 to 100 m²/g pH: 3 to 6, as measured in 4% aqueous dispersion of said granules Compacted density: 400 to 1,200 g/l.

2. A process for preparing granules according to claim 1, comprising:

dispersing pyrogenic titanium dioxide in water to form a dispersion, and spray-drying the dispersion of titanium dioxide.

3. Granules comprising pyrogenic titanium dioxide with the following physico-chemical characteristics:

Average particle diameter: 10 to 160 μm

BET surface area: 15 to 100 m²/g pH: 3.0 to 9.0, as measured in 4% aqueous dispersion of said granules

TABLE 4

Physico-chemical data of hydrophobized titanium dioxide granules in accordance with Example 6

| Example | BET surface area [m²/g] | Carbon content [%] | Compacted density [g/l] | PH | Loss on drying [%] | Loss on ignition [%] | $d_{50}$ value (Cilas) [μm] |
|---|---|---|---|---|---|---|---|
| 10 | 36 | 3.9 | 848 | 3.1 | 0.2 | 4.2 | 29.8 |
| 11 | 30 | 5.5 | 873 | 3.2 | 0.4 | 6.1 | 28.7 |
| 12 | 32 | 2.1 | 768 | 3.6 | 0 | 1.9 | 30.2 |
| 13 | 25 | 3.3 | 883 | 3.9 | 0 | 4.4 | 28.1 |

Compacted density: 400 to 1,200 g/l Carbon content: 0.3 to 12.0 wt. %.

4. A process for preparing granules according to claim 3, comprising:

dispersing pyrogenic titanium dioxide in water to form a dispersion, spray-drying the dispersion of titanium dioxide, and silanizing the spray-dried titanium oxide.

5. A process according to claim 4, wherein the silanizing is carried out using at least one member selected from the group consisting of halogenated silanes, alkoxysilanes, silazanes, and siloxanes.

6. A process according to claim 5, wherein the silanizing is carried out using trimethoxyoctylsilane as a silanizing agent.

* * * * *